United States Patent [19]

Schmid

[11] Patent Number: 4,556,367
[45] Date of Patent: Dec. 3, 1985

[54] SOLVENT DELIVERY SYSTEM
[75] Inventor: Carl E. Schmid, Easton, Conn.
[73] Assignee: The Perkin-Elmer Corporation, Norwalk, Conn.
[21] Appl. No.: 632,758
[22] Filed: Jul. 20, 1984

Related U.S. Application Data

[63] Continuation of Ser. No. 343,807, Jan. 29, 1982, abandoned.
[51] Int. Cl.⁴ .......................... F04B 3/00; F04B 49/06
[52] U.S. Cl. ...................................... 417/18; 417/265; 417/267
[58] Field of Search ................. 417/538, 18, 265, 266, 417/267; 92/84

[56] References Cited

U.S. PATENT DOCUMENTS

| | | | |
|---|---|---|---|
| 1,261,061 | 4/1918 | Seymour | 417/267 |
| 1,327,272 | 1/1920 | Dellgren | 92/84 |
| 3,323,461 | 6/1967 | Bennett | 417/478 |
| 3,816,029 | 6/1974 | Bowen | 417/339 |
| 4,067,666 | 1/1978 | Richards | 417/265 |
| 4,128,476 | 12/1978 | Rock | 201/101 |
| 4,173,437 | 11/1979 | Leka | 92/168 |
| 4,236,877 | 12/1980 | Curtis | 417/265 |
| 4,352,636 | 10/1982 | Patterson et al. | 417/265 |

FOREIGN PATENT DOCUMENTS 763846 12/1956 United Kingdom ................ 417/538

Primary Examiner—William L. Freeh
Attorney, Agent, or Firm—F. L. Masselle; E. T. Grimes

[57] ABSTRACT

A solvent delivery system which provides a substantially uniform flow includes two synchronized pistons adapted to serially transport successive solvent compositions from one piston to the other prior to delivery to a chromatography column.

17 Claims, 10 Drawing Figures

SOLVENT DELIVERY SYSTEM

BACKGROUND OF THE INVENTION

This is a continuation of co-pending application Ser. No. 343,807 filed Jan. 29, 1982 now abandoned.

The present invention generally relates to a solvent delivery system and, in particular, relates to such a system including two synchronized pistons adapted to serially transport solvent mixtures of successively varying composition to a chromatographic fractionating column.

The advent of solvent gradient analysis in the field of liquid chromatography has resulted in the need for improved delivery systems, i.e., means for delivering solvent mixtures, or compositions, from a solvent reservoir to the chromatographic column. The major difficulty is to satisfy the requirements for varying the solvent composition while delivering a small volume thereof to the column; to select low stable percentage composition levels; and to maintain a uniform flow rate to the column while column pressure changes. To date, these requirements have been difficult to satisfy simultaneously with either "pre-pump gradient systems" or "post-pump gradient systems".

A conventional post-pump gradient forming system generally includes a separate pump and motor for each solvent. Because the flow rate of each pump varies during each cycle of the pump, such systems require a mixer to smooth out the composition variations which occur where the two solvent streams are joined. The inclusion of such a mixer is undesirable because it increases the volume of the system and thus the time required to change composition levels. A further problem is that solvents having different viscosities and compressibilities are often used to form a single solvent composition. When the solvent composition is changed, the column pressure changes which in turn changes the flow rate of one or more of the solvents, i.e., each pump operates under the same pressure change, and thus the volume of each solvent pumped will depend upon its compressibility. Thus, each solvent has a different flow rate and consequently, the solvent composition is always somewhat in error.

A conventional pre-pump gradient system generally includes a single motor and pump. In such a system the solvent composition is determined by low pressure valves the degree or duration of opening of which select solvent combinations and proportions during the refill stroke of the delivery piston. One inherent disadvantage of such a system is the conflicting requirements it imposes on the time allowed to refill the delivery piston cylinder. The conflicting requirements are that to maintain uniform flow to the column it is required to minimize refill time, but reducing the refill time increases the requisite average flow rate through the solvent selector valves to a level where the finite valve switching time limits the minimum controllable volume and hence the minimum controllable composition level. Additionally, valve switching is complicated by the non-linear flow of solvents through the valves during refill.

One practical solution is a delivery system which includes a pulse damper and a discrete mixing chamber and which employs correction curves relating valve programming to particular solvent compositions.

SUMMARY OF THE INVENTION

Accordingly, one object of the present invention is to provide a solvent delivery system which maintains a substantially uniform solvent delivery flow of selected component solvents without the need for a discrete mixer.

Another object of the present invention is to provide such a solvent delivery system which is time independent of the valves controlling the flow of the individual solvents.

These objects are achieved, at least in part, by a solvent delivery system including two synchronized pumps adapted to serially transport fixed or successively varying solvent compositions from one pump to the other pump prior to delivery to a fractionating column.

Other objects and advantages will become apparent to those skilled in the art from the following detailed specification taken in conjunction with the appended drawing.

BRIEF DESCRIPTION OF THE DRAWING

The drawing, which is not to scale, includes:

FIG. 1A, which is a profile of a cam useful in the system of FIG. 1; and

DETAILED DESCRIPTION OF THE INVENTION

Figure 1:
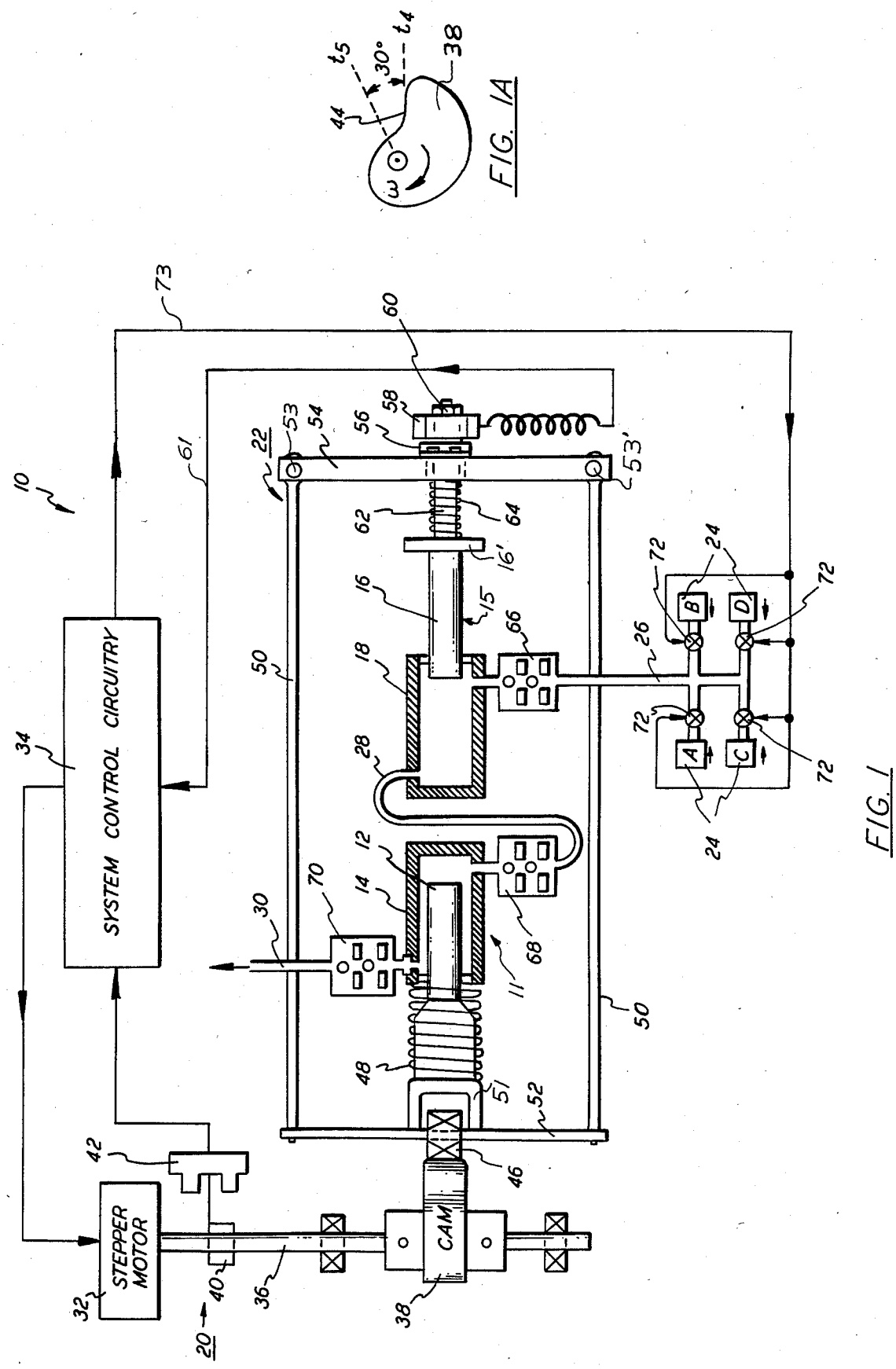
FIG. 1, which is a schematic representation of a solvent delivery system embodying the principles of the present invention.

A solvent delivery system, indicated generally at 10 in the drawing and embodying the principles of the present invention, includes a positive displacement delivery pump 11 having a piston 12 reciprocatable in a cylinder 14 associated therewith and a metering pump 15 having a piston 16 reciprocatable in cylinder 18 associated therewith. Cylinders 14 and 18 are fixedly disposed relative to one another with their respective axes of reciprocation aligned. The system 10 further includes means 20 for driving and controlling the movement of the pumping or delivery piston (12), as well as means 22 for passively synchronizing the movement of the metering piston 16 to the movement of the pumping piston 12. Specifically, means 22 takes the form of a yoke which establishes a lost motion connection between metering piston 16 and delivery piston 12 in a manner hereinafter described. The system 10 further includes a plurality of solvent sources 24, or reservoirs, individually designated as A, B, C and D and unidirectional flow conduit means 26, 28 and 30 for conveying solvents, respectively, from the reservoirs 24 to the metering pump cylinder 18, from the metering pump cylinder 18 to the delivery pump cylinder 14, and from the delivery pump cylinder 14 to a chromatography column (not shown). Thus it will be seen that pumps 11 and 15 are hydraulically coupled by conduit means 28 and operate in 180° phase opposition to one another.

In a particular embodiment, the means 20 for driving and controlling the movement of delivery piston 12 includes a stepper motor 32 which rotates through a predetermined angle in response to each electrical pulse provided thereto. Stepper motors are well known in the electrical art, and a detailed description thereof is deemed unnecessary herein. However, in this exemplary embodiment the stepper motor 32 is designed to have 400 steps for each complete rotation. Further, it is preferred that the stepper motor 32 be provided with an electrical signal having a maximum frequency of 5000 pulses per second. Thus, the stepper motor 32 rotates at a maximum speed of 12.5 revolutions per second. The electrical signal is provided by system control circuitry 34. The system control circuitry 34 referred to herein is described in detail in U.S. Pat. No. 4,450,574 issued on co-pending patent application Ser. No. 343,805 entitled "Control Circuit For Liquid Chromatograph", filed Jan. 29, 1982, assigned to the assignee hereof, and which is incorporated by reference herein.

A shaft 36 is rotatively driven by stepper motor 32 through a four-to-one reduction mechanism (not shown) and carries a cam 38 and a shaft position indicator 40. The shaft position indicator 40 provides a signal, via a transducer 42, for example, to the control circuitry 34 for use thereby in coordinating the system operation. The cam 38 has a profile 44, i.e., a peripheral contour, as shown in FIG. 1A. The cam 38 is contacted by a cam follower such as roller 46 which is adapted to translate the rotational movement of the cam 38 into linear reciprocation of the pumping piston 12 within the delivery pump cylinder 14. A biasing means such as compression spring 48 acting between piston 12 and cylinder 14 maintains the cam follower 46 against the cam 38.

Although discussed in greater detail in the above-mentioned U.S. Pat. No. 4,450,574, it should be noted herein that the electrical signal from the transducer 42 associated with the shaft position indicator 40 can be used as a pumping piston position indicator for the control circuitry 34.

As previously mentioned, metering pump piston 16 is passively synchronized with delivery pump piston 12 by means 22 which in this embodiment takes the form of a quadrangular yoke, made up of a pair of tie rods 50, 50' extending parallel to and equally spaced on opposite sides of the aligned axes of cylinders 14, 18, and parallel transverse links 52, 54. Link 52 has its ends connected to corresponding ends of tie rods 50, 50' and its mid-portion journaled in a trunnion-like structure 51 on the crank end of piston 12 so as to form an axle for cam-following roller 46.

Link 54 has its ends pivotally connected as at 53, 53' to the corresponding ends of tie rods 50 so that its midportion intersects the coincident reciprocational axes of piston 12, 16. An axial extension 62 on the crank end of piston 16 extends through and is journaled in link member 54. Secured to the free end of extension 62, as by means of a nut 60, is one contact element 58 of an electrical switch. The other contact 56 of the switch is mounted on the surface of link member 54 facing contact 58 which is considerably larger in cross-section than extension 62. Thus displacement of extension 62 in its journal in member 52 to the left (as viewed in FIG. 1) is limited by engagement of contact 58 with contact 56 to transmit an electrical signal to the control circuitry 34 via a conductor 61. A compression spring 64 or like resilient biasing means acts between link 54 and a spring abutment collar 16' on piston 16 to urge the piston and link in a direction to close contacts 56, 58; displacement in the opposite direction is resisted by the force of spring 64 and the pressure of fluid in cylinder 18 as will become more fully apparent as this description proceeds. Thus it will be seen that yoke 22 has a direct mechanical connection to delivery piston 12 and a lost motion connection to metering piston 16.

Due to this arrangement and by appropriate selection of the strength of spring 64, when piston 12 is on its inward or compression stroke (to the right in FIG. 1) abutment of contact 56 with contact 58 causes piston 16 to follow; on the reverse stroke yoke 22 moves leftward with piston 12 but, assuming that cylinder 18 is filled—as of course it would be in operation—with the working fluid (viz., the solvent composition), piston 16 does not begin its inward (i.e., leftward) travel until spring 14 is compressed to the point where the force it exerts on piston 16 through abutment collar 16' is sufficient to overcome the pressure of the fluid in the cylinder (assumed to be 100 p.s.i. for purposes of example). The point at which this occurs is a function of the operating pressure and compressibility of the particular solvent composition occupying cylinder 14 on the previous stroke. It will be seen that with more compressible compositions, piston 16 will move farther inwardly (to the left) compressing the solvent until its pressure exceeds the force of spring 64. Consequently, the quantity of fluid transferred from metering pump cylinder 18 to delivery pump cylinder 14 is equal to the volume which was expelled by the delivery pump on the previous stroke and is measured at a constant pressure, independently of head clearance volume, delivery pressure and differences in compressibility of the particular, and varying, solvent compositions.

When the reverse stroke begins, i.e., when the delivery pump piston starts its inward travel (to the right in FIG. 1), the yoke 22 simultaneously starts its travel to the right; however, piston 16 remains stationary until contact 56 engages contact 58. This marks the start of the solvent delivery intake to the metering cylinder 18; the closure of the electrical switch contacts 56, 58 signals the precise moment of the event to control circuit 34 via conductor 61. The signal is designated at $t_2$ of FIG. 2c. The end of flow is marked at $t_4$, FIG. 2C, at which point the cam 38 has reached its high point. This point is marked electrically by sensor 42. Thus, the volume entering the metering piston cylinder is available as an electrical analog to be computed by the system control circuitry 34 from the number of steps representing position of the metering piston 16 occurring within the signal transitions $t_2$ and $t_4$. This volume, so derived, is the analog of the volume at 100 p.s.i. of mixture which left the pumping piston cylinder 14 on the previous stroke. The availability of this analog volume signal allows the system control circuitry 34, for instance, to program the valves A, B, C and D, FIGS. 2D through 2G, such that the number of stepper motor 32 pulses any one valve is open ($N_A$) as compared to the current number of stepper motor pulses between $t_2$ and $t_4$ ($N_T$) is the desired $N_A$. That is %A=$N_A/N_T$ and the composition so generated is independent of the column back pressure. Furthermore, the accumulation of $N_T$ is a direct analog of the total volume of mixture referred to 100 p.s.i. which leaves the solvent delivery system. This analog signal is available to define column retention volume for eluting peaks.

In order to make certain that the quantity of fluid transferred from metering cylinder 18 to delivery pump 14 is sufficient to fill the latter completely, as well as to insure opening of contacts 56, 58, the diameter of the metering cylinder is somewhat larger than that of the delivery system.

As previously mentioned, conduits 26, 28 and 30 are unidirectional in nature; this is accomplished, for example, by their inclusion of respective ball check assemblies 66, 68, 70 located and arranged so that conduit 26 accommodates flow in a single direction from solvent sources 24 to cylinder 18; conduit 28 from cylinder 18 to cylinder 14 and conduit 30 from cylinder 14 to the fractionating column (not shown).

Each of the solvent sources 24A–24D is in flow communication with conduit 26 through respective electrically-operated valves 72 which receive control signals via a conductor 73 from system control circuitry 34, the time and/or degree of opening and closing determining the composition of the solvent mixtures supplied to the delivery system. As will be more fully explained presently in connection with a description of the system's operation, valves 72 are opened and closed entirely during the intake stroke of the metering pump piston 16 rather than the refilling stroke of the delivery pump piston 14; consequently, the duration of the refill stroke of the delivery pump (the non-pumping time) can be very brief (a small fraction of a complete pump cycle) without the constraints imposed by valve switching speeds, solvent flow rates, etc. The brief duration of the refill stroke of the delivery piston is reflected in the profile of cam 38 as shown in FIG. 1A wherein it is shown to occur in the 30° interval between $t_4$ and $t_5$ as will be more fully explained in conjunction with a description of the system operation.

Figure 2:
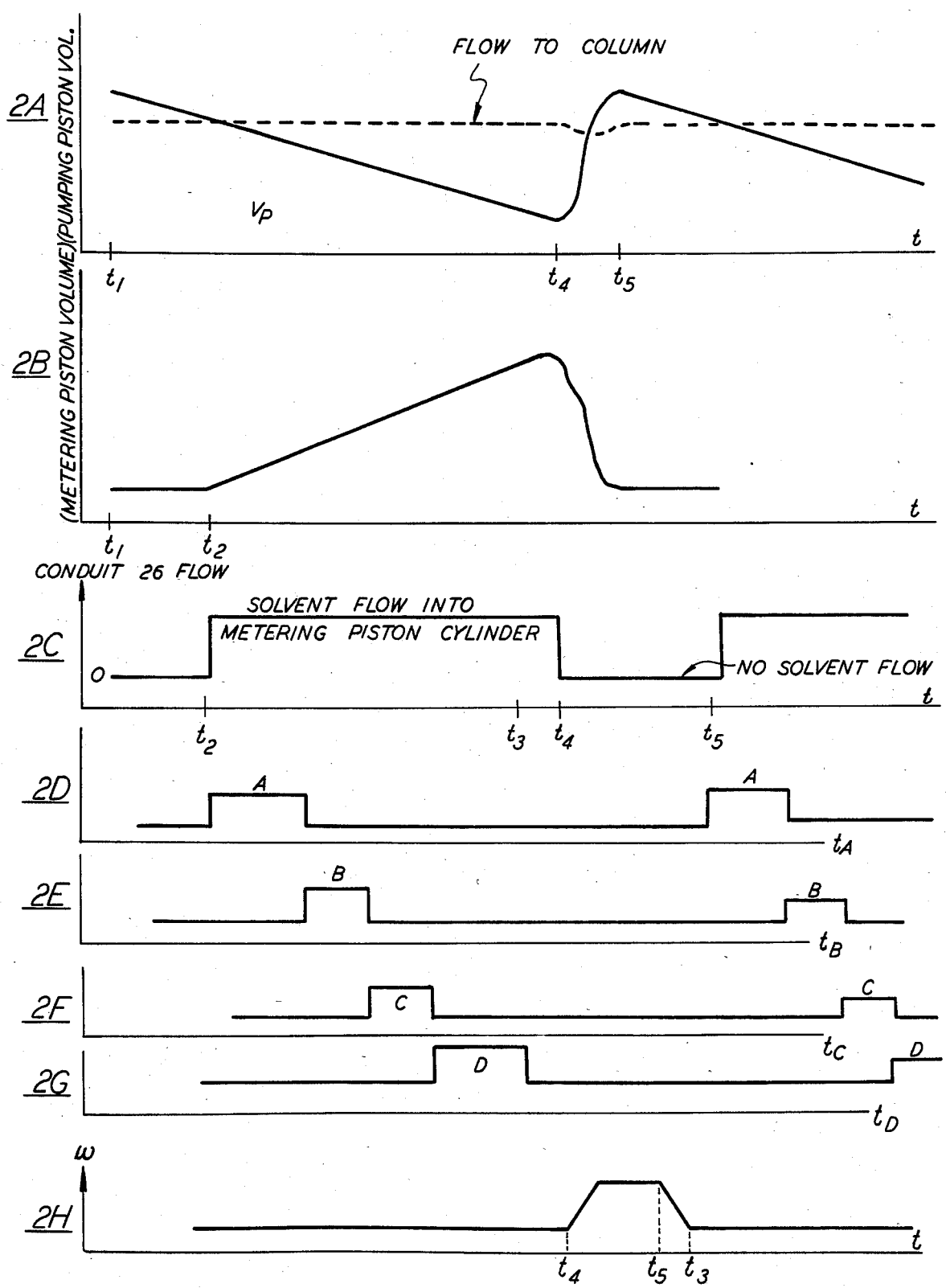
FIGS. 2A-2H, which are timing diagrams showing the dynamic relationship between the elements of the system shown in FIG. 1.

Referring now to the timing diagrams of FIG. 2, the operation of the system 10 will be discussed in detail. Specifically, as shown in FIGS. 2A and 2B at $t_1$, the delivery pump cylinder 14 has a fluid volume $V_P$ therein which is at its maximum and, as shown in FIG. 2B, the volume $V_M$ in the metering pump cylinder 18 is at its minimum. At time $t_1$, the delivery piston 12 begins motion into cylinder 14 to empty the contents thereof into the column; the metering piston 16 initially remains stationary as the gap between contacts 56 and 58 narrows while the pressure in the metering cylinder 18 remains essentially constant until time $t_2$ when contact 56 touches contact 58 initiating the uniform retraction of the metering piston 16 and simultaneously providing a continuity signal. The metering piston retracts at a uniform rate until $t_4$, at which time the cam profile 44 is at its highest point, the metering pump cylinder 18 is completely filled and the delivery pump cylinder 14 is completely emptied.

The delivery piston 12 then withdraws and the metering piston 16 transfers the solvent at positive pressure from the metering pump cylinder 18 to the delivery pump cylinder 14 between $t_4$ and $t_5$. The short time interval, $t_4$ to $t_5$, is achieved by employing a cam profile as shown in FIG. 1A and programming the stepper motor angular velocity profile as shown in FIG. 2H. The combination of these two factors results in a very short delivery cylinder 14 refill time. Also, during the delivery cylinder refill period, $t_4$ to $t_5$, the contact 56 separates from contact 58 compressing spring 64 when the hydraulic pressure in metering pump cylinder 18 equals the value, assumed as 100 p.s.i., determined by spring 64. At this point, the deceleration of the cam angular speed $\omega$ has settled out to the nominal steady state value dictated by the desired flow. FIG. 2H shows the transient is completed at $t_3$ and FIG. 2C shows solvent flow into the metering pump 15 begins at $t_6$ where $\omega$ is stable.

FIGS. 2D through 2G are representations of solvent flow from each of the solvent sources 24 during the time interval $t_2$ to $t_4$. Preferably, the sources 24 all are under the same pressure, which is relatively low, i.e., up to about 5 p.s.i. This pressure is much larger than the pressure drop caused by the flow into the metering pump cylinder 18 passing through valves 72, conduit 26 and input check valve 66. As a result, the flow into the metering pump cylinder 18 occurs at a slow uniform rate dictated by the metering piston 16 velocity and at a low fixed pressure of approximately 5 p.s.i. throughout. Thus, mixing occurs at constant pressure and constant flow and is independent of column pressure drop.

In actual practice, the metering pump inlet check valve 66 requires a small but finite reverse flow to occur before closing. To prevent this transient from damaging the solvent control valves 24 and to improve the low level composition performance, the system control circuitry 34, preferably adjusts the solvent selector valves 72 so that the majority solvent valve is open during the transitions at $t_2$ and $t_4$ and remains open during the interval from $t_4$ to $t_6$ even though no flow occurs for the majority of the $t_4$ and $t_6$ interval. Thus, one solvent selector valve 24 is always open. Also, in practice, the inlet flow to the metering pump cylinder 18 is free of transients for valves 24 that are programmed to open at a phase removed from the ends $t_2$ and $t_4$. For this reason, it is preferred that the system control circuitry open the smallest fraction solvent valves (as shown by 2E and 2F) near the middle of the $t_2$ and $t_4$ refill interval.

The major advantage of the solvent delivery system 10 described herein can be recognized from the dotted line shown in FIG. 2A which represents the flow to the column from the system 10. As shown, the column flow is substantially constant, which is ideal in liquid chromatography. In fact, the only deviation from the uniform flow occurs during transfer of the solvent composition from the metering cylinder 18 to the pumping cylinder 14. This, of course, has been minimized by providing a positive pressure means of transferring the mixture from the metering pump cylinder 18 to the delivery pump cylinder 14. In practice, the transfer time is limited by the dynamic response of the stepper motor.

Mixing of the components of the solvent composition occurs not only from the serial delivery thereof into the metering cylinder but also from the delivery thereof to the delivery pump cylinder 14. Further mixing occurs when the solvent composition is pumped from the delivery pump cylinder 14. Thus, the solvent composition is thoroughly mixed without the need for a discrete solvent mixing apparatus.

Although a specific example has been described herein, other configurations are anticipated which do not deviate from the present invention. Hence, the description herein is deemed as exemplary and not as limiting, and the present invention is considered to be limited only by the claims appended hereto and the reasonable interpretation thereof.

What is claimed is:
1. A fluid pumping system comprising:
   a. a positive displacement delivery pump including a cylinder, a piston disposed for reciprocation in the cylinder and means defining inlet and outlet flow passages in communication with said cylinder;
   b. drive means, including a motor, for imparting reciprocative motion to said piston characterized by a relatively slow advance stroke and rapid retraction stroke;

c. a positive displacement metering pump including a cylinder, a piston disposed for reciprocation in said cylinder and means defining inlet and outlet flow passages in communication with the cylinder;

d. unidirectional flow passage means hydraulically coupling the outlet flow passage of said metering pump cylinder to the inlet flow passage of said delivery pump;

e. electrically-actuated, fluid composition control valves selectively operable to control flow of fluid into said metering pump cylinder;

f. means including a lost motion coupling between the respective pistons of said pumps for imparting reciprocative motion to said metering pump piston 180° out of phase with the piston of said delivery pump, said lost motion coupling accommodating limited relative displacement between said pistons at the start of the retraction stroke of said metering pump piston, said lost motion coupling further including an electrical switch for controlling said motor, closure of which limits said relative motion to signal the start of said retraction stroke; and g. system control circuitry means coupled to receive electrical signals including said switch closure signal to effect control of said valves.

2. A fluid pumping system according to claim 1 wherein the volumetric displacement of said metering pump slightly exceeds that of the delivery pump.

3. A fluid pumping system according to claim 2 wherein said drive means includes a cam and said motor is a stepper motor driving said cam, and said system control circuitry means controls the rate of rotation of said motor.

4. A fluid pumping system according to claim 3 wherein said system control circuitry means is programmed to accelerate the rotational speed of said motor during the retraction stroke of the delivery pump piston.

5. A fluid pumping system comprising:
a. a positive displacement pump including a cylinder and a piston reciprocatable therein;
b. drive means, including a motor, operatively coupled to impart reciprocating motion to said piston;
c. a second positive displacement pump including a cylinder and a piston reciprocatable therein;
d. linkage means between the respective pistons of said pumps effective to impart reciprocative motion to the second pump piston 180° out of phase with the first pump piston, said linkage means including a lost motion connection permitting limited displacement of one of said pistons relative to the other at the start of the retraction stroke of said second pump piston, said lost motion connection including an electrical switch having contacts engageable to define the limit of the lost motion displacement in one direction at the start of the retraction stroke of said second pump piston, the engagement of said contacts electrically signaling the start of said stroke;
e. unidirectional fluid flow means hydraulically coupling said cylinders to enable flow from said second pump to said first pump;
f. unidirectional fluid flow outlet means for said cylinder of said first pump;
g. unidirectional fluid flow inlet means for the cylinder of said second pump and including electrically-actuated fluid composition control valves operable to control flow of fluid through said inlet means; and
h. system control circuitry means coupled to receive electrical signals including said start-of-stroke signal to effect control of said valves.

6. A fluid pumping system according to claim 5 wherein said lost motion connection further includes resilient means biasing such displacement in the opposite direction with a force determinative of the pressure of fluid in the cylinder of said second pump during the advance stroke of the piston therein.

7. A fluid pumping system according to claim 6 wherein said drive means includes a cam driven by said motor having a profile determinative of the displacement pattern of the piston of said first pump, said profile causing rapid retraction of said first pump piston occurring over a very minor fraction of a single revolution of said cam and a relatively slower and uniform rate of travel during the advance stroke of said piston.

8. A fluid pumping system according to claim 7 wherein said drive means motor is a stepper motor and said system control circuitry means is programmed to accelerate the rate of rotation of said cam during said retraction stroke of the first pump piston.

9. A solvent delivery system for high pressure liquid chromatograph comprising:
a. a positive displacement delivery pump including a cylinder and a piston reciprocatable therein;
b. a cam shaft rotatively journaled with its longitudinal axis intersecting, substantially at right angles, the axis of reciprocation of said piston;
c. a cam fixed to said cam shaft with its camming surface disposed to advance and retract said piston in said cylinder, the profile of said camming surface being such that the angular extent of the surface causing advance of the piston is several times greater than that causing retraction;
d. stepper motor means coupled to rotate said cam shaft;
e. a positive displacement metering pump including a cylinder and a piston reciprocatable therein, said delivery and metering pumps having their respective cylinders fixedly disposed relative to one another with their respective axes of reciprocation aligned;
f. a coupling yoke constructed and arranged to effect reciprocation of the metering pump piston 180° out of phase with the delivery pump piston, said yoke having a positive connection to the piston of the delivery pump and a lost motion connection to the piston of the metering pump, said lost motion connection permitting limited relative displacement of said pistons at the start of both the retraction and advance strokes of the metering pump piston;
g. an electrical switch having respective electrical contact members on said yoke and the metering pump piston disposed for abutment to define the limit of lost motion travel in one direction between said yoke and piston and close the switch to signal the start of the retraction stroke of said metering pump piston;
h. resilient bias means acting between said yoke and metering pump piston to urge said yoke and piston toward said limit with a force determinative of the pressure of fluid in the metering pump cylinder at the start of the advance stroke of the metering pump piston;

i. unidirectional flow passage means hydraulically coupling the cylinders of said pumps to permit transfer of fluid from the metering pump cylinder to the delivery pump cylinder;

j. sensor means effective to detect the angular position of said cam and signal the end of the retraction stroke of the metering pump piston; and k. system control circuit means electrically coupled to receive signals from said electrical switch and from said sensor means and generating output signals controlling said stepper motor.

10. A solvent delivery system according to claim 9 further comprising:

a. means defining a second unidirectional flow passage enabling inward flow to said metering cylinder;

b. a plurality of sources of selected solvents and flow passage means connecting said sources to said second unidirectional flow passage;

c. respective electrically-actuated valves operable to control flow from said sources to said second unidirectional flow passage; and d. means electrically connecting said valves to receive a control signal from said system control circuitry.

11. A solvent delivery system according to claim 10 wherein said system control circuitry is programmed to open said electrically actuated valves only during the retraction stroke of the metering piston.

12. A solvent delivery system according to claim 11 wherein said system control circuitry is programmed to accelerate the angular velocity of said cam during the retraction stroke of said delivery pump piston.

13. A fluid pumping system comprising:

a. a positive displacement delivery pump including a cylinder and a piston reciprocatable therein;

b. drive means, including a stepper motor, operatively coupled to impart reciprocating motion to said piston;

c. a positive displacement metering pump including a cylinder and a piston reciprocatable therein, said cylinder having a unidirectional fluid flow inlet means;

d. electrically-actuated fluid composition control values selectively operable to control fluid flow through said inlet means;

e. linkage means forming a lost motion connection between the respective pistons of said pumps effective to drive the metering pump piston to reciprocation 180° out of phase with the delivery pump piston and including resilient bias means effective to permit limited displacement of one of said pistons relative to the other;

f. unidirectional fluid flow means hydraulically interconnecting the respective cylinders of said pumps to enable transfer of fluid from the metering pump to the delivery pump;

g. electrical switch means coupled to said valves and closed by the relative lost motion displacement of said piston at the start of the retraction stroke of the metering piston; and h. sensor means coupled to said motor to generate an electrical signal at the end of the retraction stroke of said metering pump piston.

14. A fluid pumping system according to claim 13 wherein said drive means includes a cam driven by said stepper motor and system control circuitry electrically connected to receive signals from said sensor means and said electrical switch means to control the operation of said stepper motor and said valves.

15. A fluid pumping system comprising:

a. a positive displacement delivery pump including a cylinder, a piston disposed for reciprocation in the cylinder and means defining inlet and outlet flow passages in communication with said cylinder;

b. drive means including a motor for imparting reciprocative motion to said piston characterized by a relatively slow advance stroke and rapid retraction stroke;

c. electrically-actuated fluid composition control valves; and d. metering pump means having a unidirectional inlet controlled by said valves and operative in timed relation to the reciprocation of said piston for measuring a volume of fluid at constant pressure and transferring the measured volume to said delivery pump during said retraction stroke, said metering pump means including respective electrical switch and sensor means to generate electrical signals for control of said motor and said valves, said signals precisely coinciding with the start and finish of said retraction stroke.

16. A fluid pumping system according to claim 15 wherein said metering pump means comprises:

a. a second positive displacement pump including a cylinder, a piston disposed for reciprocation in the cylinder and means defining inlet and outlet flow passages in communication with the cylinder;

b. unidirectional flow passage means hydraulically coupling the outlet flow passage of said metering pump cylinder to the inlet flow passage of said delivery pump; and c. means for imparting reciprocative motion to said metering pump piston 180° out of phase with the piston of said delivery pump.

17. A fluid pumping system according to claim 16 wherein said last mentioned means (2.c.) includes a lost motion coupling between the respective pistons of said pumps, accommodating limited relative displacement therebetween at the start of the retraction stroke of said metering pump piston.

* * * * *